United States Patent
Pullela et al.

(10) Patent No.: US 8,986,976 B2
(45) Date of Patent: Mar. 24, 2015

(54) METHOD FOR ISOLATION OF NUCLEIC ACIDS AND A KIT THEREOF

(75) Inventors: Phani Kumar Pullela, Karnataka (IN); Mulakkapurath Narayanan Manoj, Karnataka (IN); Santhosh Kumar Gandhavalla, Karnataka (IN); Mitchell Preetham Pinto, Karnataka (IN); Chandrasekhar Bhaskaran Nair, Karnataka (IN); Pillarisetti Venkata Subbarao, Karnataka (IN)

(73) Assignee: Bigtec Private Limited, Bangalore, IN (US)

( * ) Notice: Subject to any disclaimer, the term of this patent is extended or adjusted under 35 U.S.C. 154(b) by 0 days.

(21) Appl. No.: 13/520,685

(22) PCT Filed: Jan. 6, 2011

(86) PCT No.: PCT/IB2011/050044
§ 371 (c)(1),
(2), (4) Date: Sep. 25, 2012

(87) PCT Pub. No.: WO2011/083429
PCT Pub. Date: Jul. 14, 2011

(65) Prior Publication Data
US 2013/0203150 A1    Aug. 8, 2013

(30) Foreign Application Priority Data
Jan. 7, 2010   (IN) ............................... 50/CHE/2010

(51) Int. Cl.
*C12N 1/08* (2006.01)
*C07H 1/08* (2006.01)
*C12N 15/10* (2006.01)

(52) U.S. Cl.
CPC *C07H 1/08* (2013.01); *C12N 15/10* (2013.01); *C12N 15/1006* (2013.01)
USPC ........................... 435/270; 435/91.1; 435/259

(58) Field of Classification Search
CPC .................... B01L 2200/025; B01L 2200/028; B01L 2400/478; B01L 2400/43; B01L 2300/27; B01L 2300/23; B01L 3/527; B01L 7/52; C12N 15/62; C12N 15/1006; C12N 15/8216; C12Q 1/68
See application file for complete search history.

(56) References Cited

U.S. PATENT DOCUMENTS

| | | |
|---|---|---|
| 5,804,684 A | 9/1998 | Su |
| 6,084,091 A | 7/2000 | Muller et al. |
| 7,217,513 B2 | 5/2007 | Parameswaran et al. |
| 7,264,927 B2 | 9/2007 | Nargessi et al. |
| 2004/0161788 A1 | 8/2004 | Chen et al. |

OTHER PUBLICATIONS

Kephart D. et al., Rapid Isolation of Genomic DNA from Small Quantities of Human Tissue, Geneprint-TM 1999, pp. 7-9, Profiles in DNA, published on the web on Feb. 1, 2001.*
Shea L.H. et al., DNA profiling on fabrics: an in-situ method, International Congress Series, 2004, vol. 1261, pp. 565-567.*
Harvey M. A., The use of filter paper to collect blood samples for diagnostic applications—a report, Accessed on Oct. 18, 2013 from the web at—http://www.acefesa.es/bio/fta/903/documentos/903.doc., pp. 1-2.*
Psifidi et al., A comparison of six methods for genomic DNA extraction suitable for PCR-based genotyping applications using ovine milk samples, Molecular and Cellular Probes, 2010, pp. 93-98, vol. 24.

* cited by examiner

*Primary Examiner* — James Martinell
(74) *Attorney, Agent, or Firm* — The Webb Law Firm

(57) ABSTRACT

The present disclosure provides a method to isolate natural & artificial nucleic acids like deoxyribonucleic acid (DNA), ribonucleic acid (RNA) and peptide nucleic acid (PNA) from a solid or liquid sample using cotton. The cotton packed is such that, a solution containing nucleic acids passes through it and the nucleic acids in solution are bound to the cotton in a medium optimal for binding. The nucleic acids are bound to cotton in such a way that, the bound nucleic acids can withstand multiple washes with liquid comprising water and gets eluted in an aqueous buffer, with which eluted nucleic acids can be directly used for amplification using PCR or for any other biochemical or molecular biology needs.

19 Claims, 8 Drawing Sheets

METHOD FOR ISOLATION OF NUCLEIC ACIDS AND A KIT THEREOF

TECHNICAL FIELD

Figure 1:
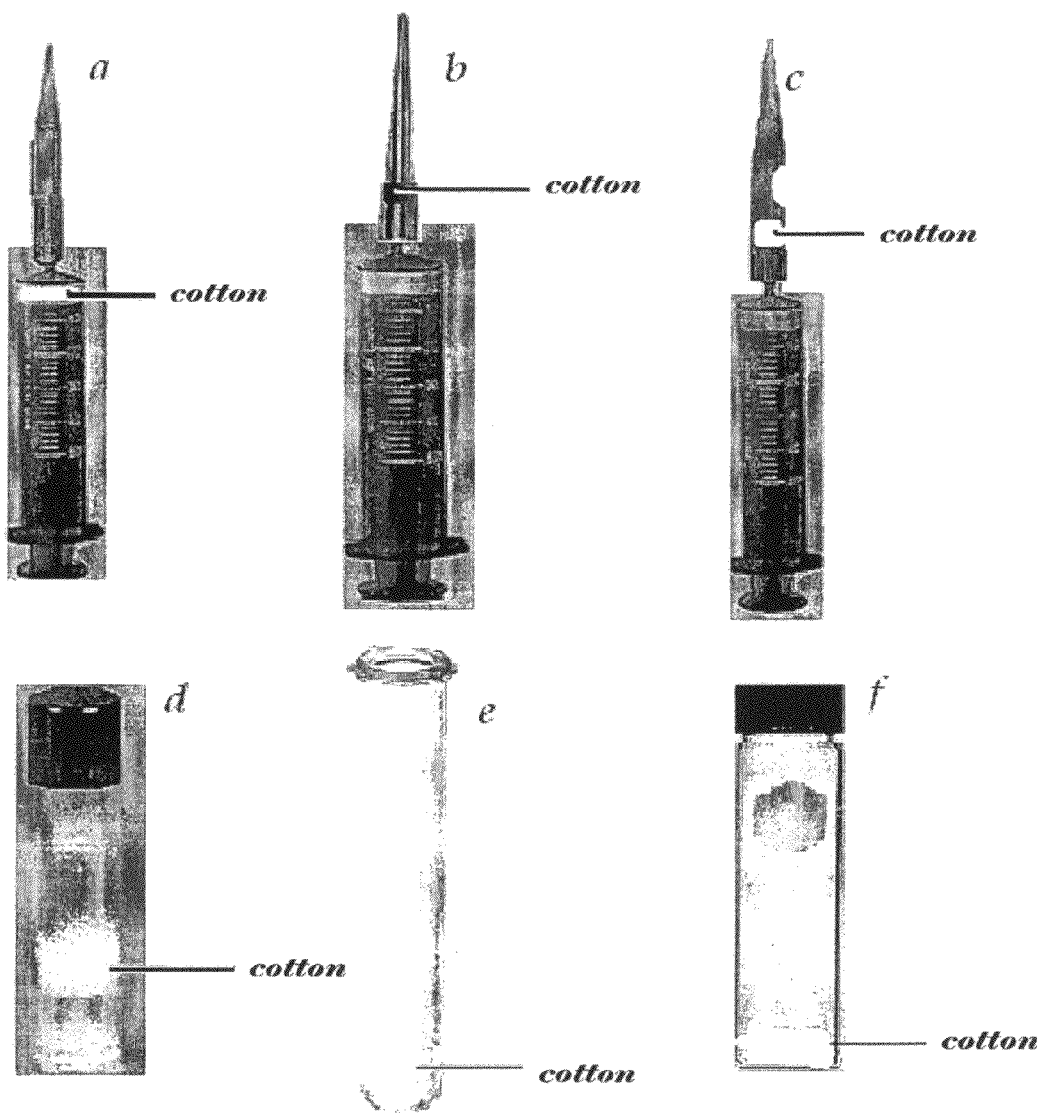

The present disclosure relates to isolation and purification of nucleic acids. More essentially, it provides a method and a kit for isolation and purification of nucleic acids using cotton or its derivatives.

BACKGROUND AND PRIOR ART OF THE DISCLOSURE

Nucleic acid extraction protocols can be broadly classified into silica based and non-silica based protocols. The existing silica and non-silica protocols cannot tolerate a water wash to remove non-nucleic acid components and require an aqueous wash with some percentage of alcohol in it. Presence of alcohol in eluted nucleic acid solution inhibits polymerase chain reaction (PCR) and hence, typically both the protocols require a high speed spinning or other methods to remove residual alcohol and elution of nucleic acids with a room temperature or elevated temperature aqueous buffer. In some cases, both the protocols require a high salt concentration with polyethylene glycol or an aqueous alcohol wash. The use of high concentration of salts and aqueous alcohol puts a restriction on the elution of nucleic acids like strict removal of these components before nucleic acids are eluted or use of centrifuge etc. Hence, none of the existing silica or non-silica based protocols can be used at point of care (POC) as a centrifuge will generate aerosols. Some of the non-silica based protocols reported in literature are given below:

U.S. Pat. No. 7,264,927: This document describes use of cellulose or cellulose paper involving use of polyalkylene glycol and high salt concentrations to bind and finally, elute the nucleic acids in a buffer or deionized water.

U.S. Pat. No. 6,084,091: Describes method of using cellulose flour (like potato starch) for nucleic acid isolation.

U.S. Pat. No. 5,804,684: Describes a method to use filter paper for nucleic acid extraction, where it is housed in a material like a plastic tip with the help of a soft tissue paper or piece of cotton as filter or barrier to support the filter paper.

All the above processes use either commercially available silica columns for final nucleic acid isolation, or require longer sample processing times (greater than 30 mins) or involve use of high concentrations of salts during washing of matrix or use of centrifuges etc. None of the cellulose based nucleic acid extraction methods wash the nucleic acids with a 100% aqueous buffer or water and usually containing a percentage of alcohols or polyol containing compounds.

STATEMENT OF THE DISCLOSURE

Accordingly, the present disclosure relates to a method for isolation of nucleic acid from a sample, said method comprising steps of: (a) adding lysis buffer to the sample containing nucleic acid to obtain a lysed solution, or (b) adding lysis buffer in combination with binding buffer to the sample to obtain a lysed solution, (c) adding a binding buffer to the solution of step (a) to bind the nucleic acid to a matrix or direct binding of the solution of step (b) to the matrix, and (d) washing and eluting the matrix bound nucleic acid to isolate and purify the nucleic acid; and a kit for isolation of nucleic acid from a sample, said kit comprising a matrix and buffers.

BRIEF DESCRIPTION OF THE ACCOMPANYING FIGURES

The features of the present disclosure will become more fully apparent from the following description and appended claims, taken in conjunction with the accompanying figures. Understanding that these figures depict only several embodiments in accordance with the disclosure, they are therefore, not to be considered limiting to its scope, as the disclosure will be described with additional specificity and detail through use of the accompanying figures:

FIG. 1: Cotton packed in [a] syringe [b] syringe needle [c] plastic moulds attached to syringe [d] screw cap plastic bottle [e] glass test tube [f] screw cap glass vial.

Figure 2:
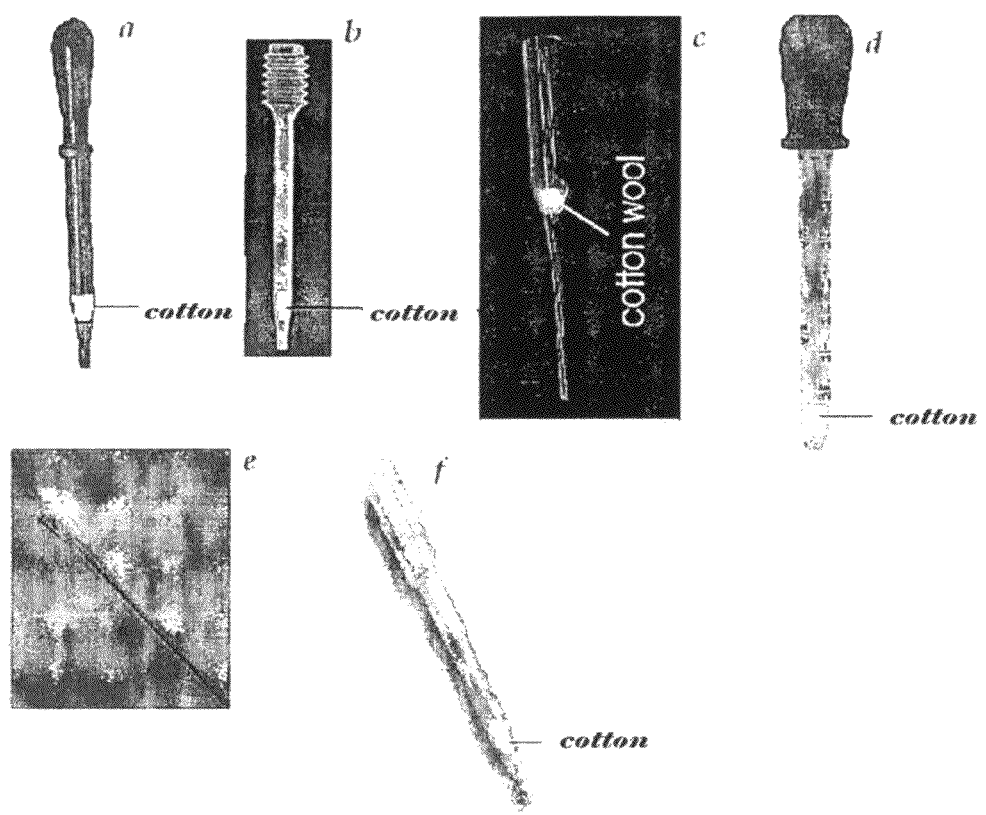

FIG. 2: Cotton packed in [a] disposable plastic dropper [b] Molded Pasteur plastic pipette [c] glass Pasteur pipette [d] plastic dropper with a rubber head [e] cotton swab [f] molded plastic pipette.

Figure 3:
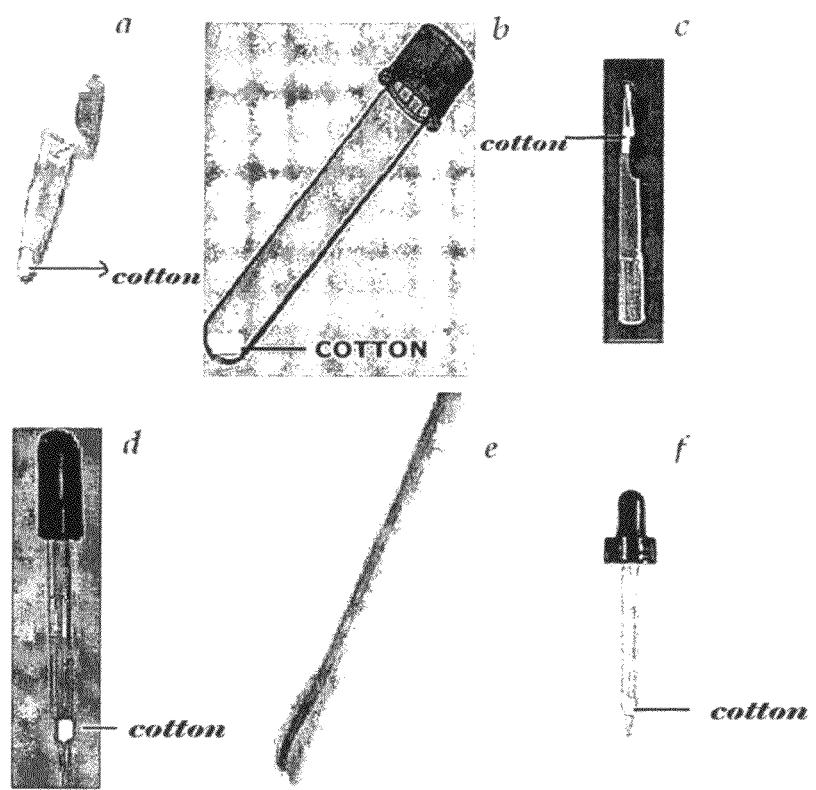

FIG. 3: Cotton packed in [a] Eppendorf tube [b] screw cap glass tube [a] molded plastic 1 mL tip [d] disposable glass graduated pipette with rubber head [e] viscose swab [f] glass pipette with a plastic and rubber head.

Figure 4:
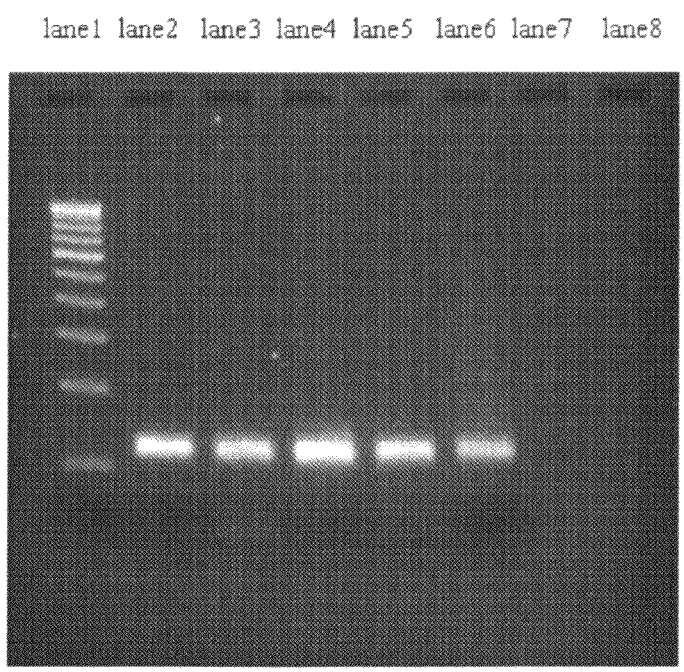

FIG. 4: DNA samples purified by different protocols were amplified by PCR. Lane 1: Molecular weight marker, lane 2: viscose packed in a 1 mL pipette tip, lane 3: commercial viscose swab, lane 4: cotton packed in 1 mL pipette tip, lane 5: commercial silica column, lane 6: DNA purified using commercial cotton swab, lane 7: unamplified DNA, lane 8: water blank.

Figure 5:
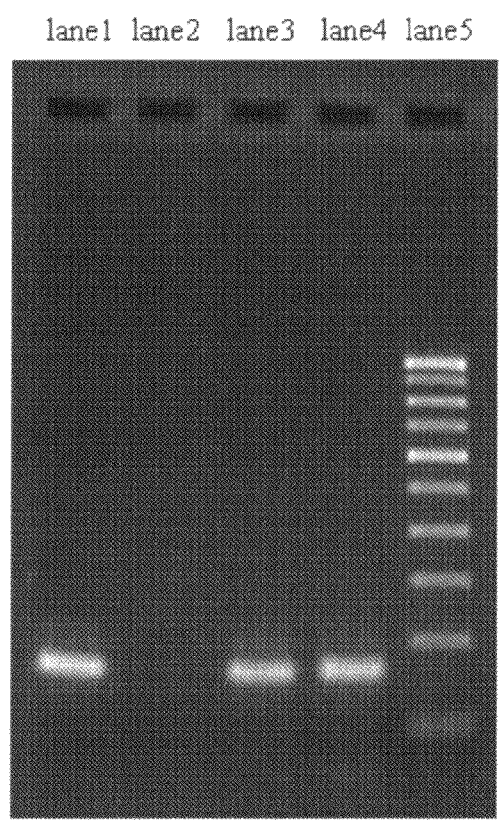

FIG. 5: DNA samples purified by different protocols were amplified by PCR. Lane 1: cotton packed in 1 mL pipette tip, lane 2: water blank, lane 3: cotton packed in 2 mL syringe, Lane 4: commercial silica column, lane 5: molecular weight marker.

Figure 6:
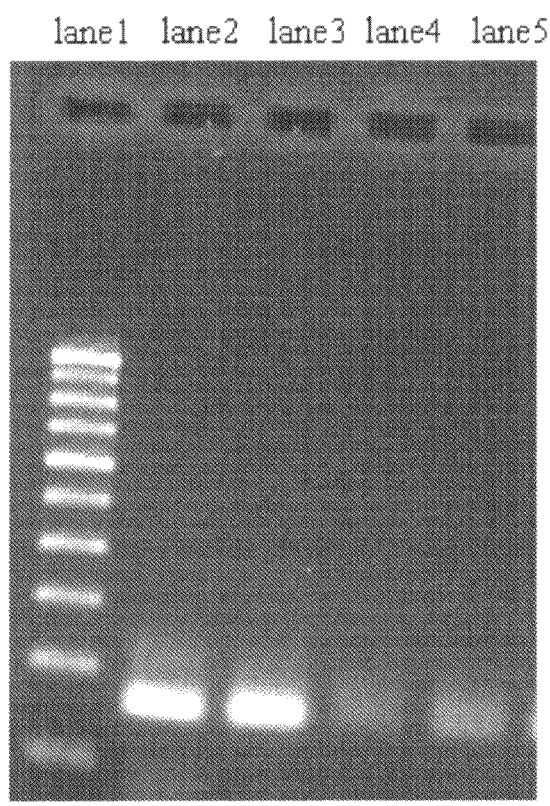

FIG. 6: DNA samples purified by different protocols were amplified by PCR. Lane 1: molecular weight marker, Lane 2: commercial silica protocol, Lane 3: Cotton packed in 1 mL pipette tip, Lane 4: Whatman No 1 filter paper packed in a pipette tip, Lane 5: FTA card protocol.

Figure 7:
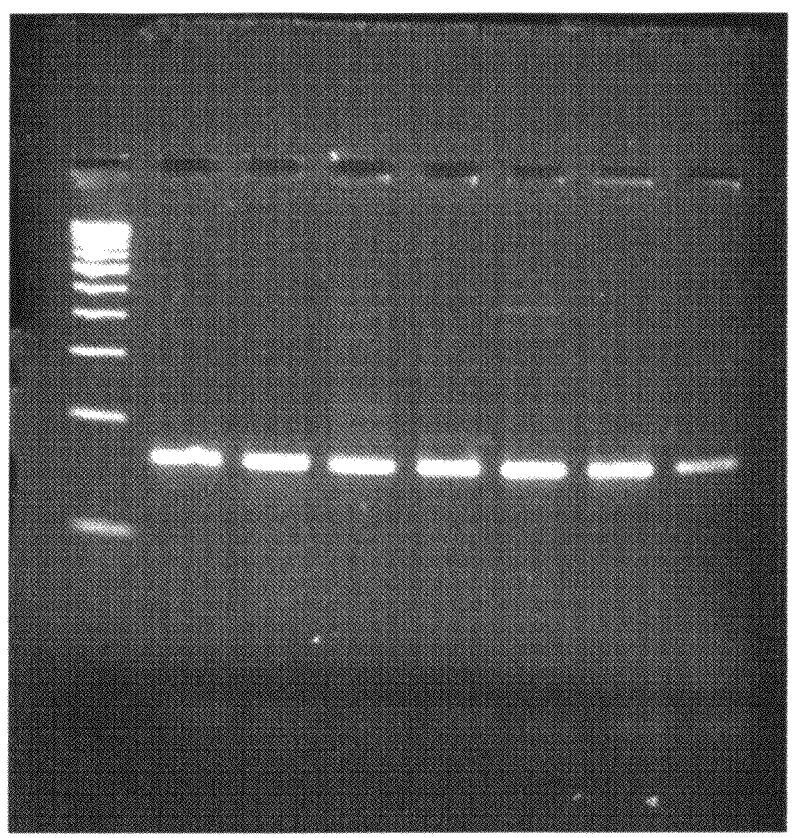
Figure 8:
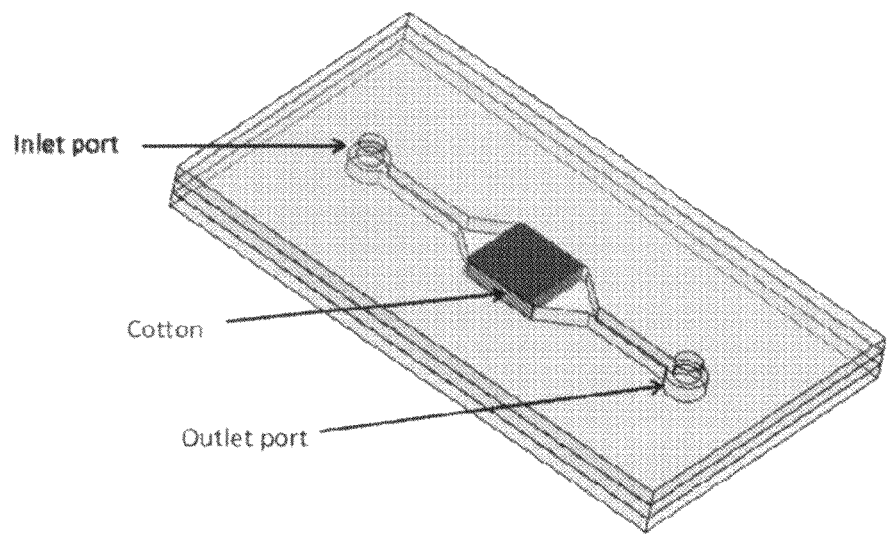

FIG. 7: A 30 ct RNA sample purified by different protocols were amplified by RT-PCR. Lane 1: Molecular weight marker, Lane 2: Surgical cotton, lane 3: Autoclaved cotton, lane 4: sodium hydroxide washed cotton Lane 5: Hydrochloric Acid washed cotton, lane 6: Absorbing cotton, Lane 7: Qiagen silica column, Lane 8: FTA card FIG. 8: A component of the cotton packed cartridge for automated nucleic acid extraction.

DETAILED DESCRIPTION OF THE DISCLOSURE

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be combined in a wide variety, all of which are explicitly contemplated and make part of this disclosure.

The present disclosure relates to a method for isolation of nucleic acid from a sample, said method comprising steps of:
(a) adding lysis buffer to the sample containing nucleic acid to obtain a lysed solution; or
(b) adding lysis buffer in combination with binding buffer to the sample to obtain a lysed solution;
(c) adding a binding buffer to the solution of step (a) to bind the nucleic acid to a matrix or direct binding of the solution of step (b) to the matrix; and (d) washing and eluting the matrix bound nucleic acid to isolate and purify the nucleic acid.

In an embodiment of the present disclosure, the nucleic acid is selected from a group comprising DNA, RNA and PNA.

In another embodiment of the present disclosure, the sample is a biological or non-biological sample.

In yet another embodiment of the present disclosure, the biological sample is selected from a group comprising blood, sputum, serum, saliva or tissue extracts and the non-biological sample is selected from a group comprising chemically synthesized PNA.

In still another embodiment of the present disclosure, the lysis buffer is selected from a group comprising guanidine thiocyanate, guanidine hydrochloride, EDTA, Tris, detergent, polyol, monovalent salt containing group IA cation or divalent salt containing group IIA cation and protein digesting enzyme optionally along with urea or any combination thereof.

In still another embodiment of the present disclosure, the EDTA is of concentration ranging from about 10 mM to about 300 mM, preferably about 100 mM.

In still another embodiment of the present disclosure, the guanidine thiocyanate or the guanidine hydrochloride is of concentration ranging from about 0.1 M to about 7 M.

In still another embodiment of the present disclosure, the urea is of concentration ranging from about 0.01 M to about 7 M.

In still another embodiment of the present disclosure, the Tris is of concentration ranging from about 0.01 mM to about 100 mM, preferably about 20 mM.

In still another embodiment of the present disclosure, the polyol is of concentration ranging from about 0.01% to about 30% (v/v).

In still another embodiment of the present disclosure, the detergent is selected from a group comprising sodium lauryl sulphate, sodium dodecyl sulphate, Triton X-100, Tween 20 and NP-40 or any combination thereof and wherein the protein digesting enzyme is proteinase K.

In still another embodiment of the present disclosure, the binding buffer is water optionally along with polyols or non-polyols.

In still another embodiment of the present disclosure, the polyol comprises water soluble polyol compounds selected from a group consisting of Poly-ethylene glycol, glycerol, Poly-propylene glycol, ethylene glycol and propylene glycol.

In still another embodiment of the present disclosure, the non-polyol comprises alcohols consisting of methanol, ethanol, propanol or any water-soluble liquid with a functional group of acid, amine, alcohol, phenol, amide or ester as one of the functional groups; or any combination thereof.

In still another embodiment of the present disclosure, the washing and eluting is carried out using washing buffer and eluting buffer respectively.

In still another embodiment of the present disclosure, the washing comprises a first wash with a washing buffer comprising about 1% to about 99% (v/v), preferably about 30% to about 70% (v/v) and optimally about 50% (v/v) of aqueous alcohol followed by multiple washes with a washing buffer comprising 100% water.

In still another embodiment of the present disclosure, the aqueous alcohol is selected from a group comprising ethanol, methanol, n-propanol, 2-propanol, glycerol, PEG, PPG, ethylene glycol and propylene glycol.

In still another embodiment of the present disclosure, the water is selected from a group comprising deionized water, DNase free water, RNase free water, MilliQ water, filtered water, tap water and ground water or any combination thereof.

In still another embodiment of the present disclosure, the said washing buffer can optionally comprise salts selected from a group comprising $MgCl_2$, $CaCl_2$, NaCl and KCl, or buffers selected from a group comprising bicine, tricine, Tris, HEPES, CHAPS, phosphate, acetate, MES, pyridine, piperazine, Bis-tris, PIPES, ACES, BES, TES, borate, TAPS, CHES, CAPS, ethanolamine and piperidine, having pH ranging from about 5 to about 12.

In still another embodiment of the present disclosure, the eluting buffer comprises warm water having temperature ranging from about 45° C. to about 99° C. along with buffer or salt, having pH ranging from about 8 to about 11.

In still another embodiment of the present disclosure, the water is selected from a group comprising deionized water, DNase free water, RNase free water, MilliQ water, filtered water, tap water and ground water or any combination thereof.

In still another embodiment of the present disclosure, the buffer is selected from a group comprising bicine, tricine, Tris, HEPES, CHAPS, phosphate, acetate, MES, pyridine, piperazine, Bis-tris, PIPES, ACES, BES, TES, borate, TAPS, CHES, CAPS, ethanolamine and piperidine or any combination thereof having pH ranging from about 5 to about 12 or having pKa ranging from about 7 to about 10.

In still another embodiment of the present disclosure, the salt is selected from a group comprising $MgCl_2$, $CaCl_2$, NaCl and KCl or any combination thereof in the concentration ranging from about 0.01 mM to about 100 mM, preferably in the range of about 5 mM to about 50 mM.

In still another embodiment of the present disclosure, the matrix is selected from a group comprising cotton, derivatives of cotton and synthetic polymers having blends of cotton or any combination thereof.

In still another embodiment of the present disclosure, the cotton is selected from a group comprising natural cotton, surgical cotton, clinical grade cotton, commercial cotton, spun cotton, water washed cotton, acid or base washed cotton, autoclaved cotton, buffer treated cotton having pH ranging from about 1 to about 14, salt solution treated cotton, organic solvent treated cotton, pressed cotton and processed cotton.

The present disclosure further relates to a kit for isolation of nucleic acid from a sample, said kit comprising a matrix and buffers.

In an embodiment of the present disclosure, the matrix is selected from a group comprising cotton, derivatives of cotton and synthetic polymers having blends of cotton or any combination thereof.

In another embodiment of the present disclosure, the cotton is selected from a group comprising natural cotton, surgical cotton, clinical grade cotton, commercial cotton, spun cotton, water washed cotton, acid or base washed cotton, autoclaved cotton, buffer treated cotton having pH ranging from about 1 to about 14, salt solution treated cotton, organic solvent treated cotton, pressed cotton and processed cotton.

In yet another embodiment of the present disclosure, the buffer is selected from a group comprising the lysis buffer, binding buffer, washing buffer and elution buffer as described above.

In still another embodiment of the present disclosure, the sample comprises biological or non-biological samples.

In still another embodiment of the present disclosure, the biological sample is selected from a group comprising blood, sputum, serum, saliva or tissue extracts and the non-biological sample is selected from a group comprising chemically synthesized PNA.

The present disclosure relates to a method for constructing a nucleic acid extraction system using cotton. The cotton is housed in a fashion where all the solutions mentioned in the nucleic acid extraction will interact with cotton.

In another embodiment, the specifications for various materials used in the instant disclosure are provided below: Cotton, Derivatives of Cotton. Materials Comprising Cotton and Cotton Like Materials:

The fluffy cotton is obtained as a boll around the cottonseed of cotton plant. For nucleic acid extraction cotton is the preferred material as matrix. The forms of cotton can be natural cotton, surgical cotton, clinical grade cotton, commercial cotton, spun cotton, water washed cotton, acid or base washed cotton, autoclaved cotton, buffer (pH 1-14) treated cotton, salt solution treated cotton, organic solvent treated cotton, pressed cotton, processed cotton etc are suitable. Any cotton fabric or different forms of cotton or synthetic polymers with blend of cotton or cotton containing materials could be used for nucleic acid extraction. Materials like wool, silk, cashmere etc, which behave fibres similar to cotton are also considered to be part of this disclosure. Cotton produced by organic farming or using insecticides and pesticides is also considered to be part of this disclosure. Cotton produced across different geographies will be slightly different in composition, structure, color and quality and it is considered that cotton grown across all regions of the world is part of this disclosure. Any product with an origin of cotton or a material, which uses cotton in its manufacture is considered to be part of this disclosure and could be used for nucleic acid extraction.

Lysis Buffer:

The lysis buffer contains a high concentration of EDTA to enable the binding of nucleic acids to cotton and also for handling different kinds of samples (blood, sputum, serum, saliva, tissue extracts etc). Variation of constituent salts is possible and the use of EDTA is given as an example and should not be consider as a limit on the disclosure. Typically any negatively charged molecule in high concentration could repel the nucleic acids in solution and enhance the binding to cotton. The lysis buffer comprises of guanidine thiocyanate or guanidine hydrochloride, EDTA, Tris, a detergent, and optionally with urea, a polyol, a monovalent salt containing group IA cation and/or a divalent salt containing a group IIA cation, and proteinase K or any protein digesting enzyme. The Guanidine thiocyanate or guanidine hydrochloride can be anywhere between 0.1 to 7 M in concentration. Guanidine thiocyanate can be replaced with guanidine hydrochloride or urea in some applications and its concentration also could vary from 0.1 to 7 M. Urea is used to denature the proteins and it will complement the function of guanidine salts and could vary between 0 to 7 M. Typically most of the literature reported lysis protocols for blood contain EDTA in the range of 1-20 mM. Our lysis buffer could contain significantly different amounts of EDTA preferably in the range of 10-300 mM, more preferably around 100 mM range. The EDTA concentration can be manipulated for other nucleic acids like RNA and PNA, but in general, a higher concentration of EDTA was found to help in improvement of cycle times (Ct) and signal intensities in PCR and RT-PCR. The significantly different concentration of EDTA helps in arresting the iron present in hemoglobin (for blood), prevents any DNase & RNase activity, and creates a highly negative atmosphere wherein nucleic acid can bind to the cotton. The important aspect of it is that, this embodiment is the first example wherein DNA binding to a matrix is done under basic conditions. Importantly, the binding pH of the solution has significant effect on DNA/RNA binding to cotton, and hence a pH around 8-10 is preferred for binding, but with a pH of 7.1-12 can be also used. Magnesium chloride is typically used in higher concentrations to deactivate RNase activity and hence, in DNA lysis protocol it is absent or used minimally (with in 20 mM). Again, the use of EDTA also deactivates RNase and the use of MgCl2 need not essential and it is optional for any nucleic acid application. Tris is the choice of buffer for lysis, and we found 0-100 mM can be used and typically around 20 mM is the optimal. This should be noted that, in our lysis buffer, Tris role is to help in the lysis and can be replaced by any suitable buffer. Use of polyol in the binding buffer is to improve the solubility of cleaved and denatured proteins. The polyol percentage in the binding buffer could be 0-30% (v/v). In some applications, a separate binding buffer is not added and after lysis, the nucleic acids were directly bound to matrix. All these buffers were typically made in deionized water and for RNA applications, the water can be optionally treated with DEPC and autoclaved. The proteinase K lysis can be done ahead of the addition of the above described lysis buffer for blood, sputum, saliva, semen etc and optionally can be done with lysis buffer. The proteinase K treatment was found to be effective in the mentioned lysis buffer and hence, this treatment can be ahead of lysis buffer addition or could be along with lysis buffer for any kind of liquid sample containing nucleic acids. The detergent used in the lysis buffer could be selected from the group comprising of SLS (sodium lauryl sulphate), SDS, Triton X-100, Tween 20, or any other commonly used ionic, nonionic detergent known in the state of art.

Binding Buffer:

Binding buffer, which was added after lysis to initiate the binding of nucleic acids with cotton was found to be very flexible in terms of composition and pH. Binding buffer is so flexible that, just addition of water is enough to dilute the concentration of salts in lysis buffer and good binding of nucleic acids to cotton was observed. Cotton can be placed to interact during the lysis or after addition of binding buffer to extract nucleic acids from the given sample. For practical purposes, binding buffer composition can be of any pH between 4 to 12, preferably in the range of 7-10. For complex samples like blood, sputum or saliva, the binding buffer can have a certain percentage of water-soluble polyol compounds like PEG, glycerol, PPG, ethylene glycol, propylene glycol etc. The PEG and PPG molecular weight could range from 200-200,000 and for all practical purposes it will be 1000 to 20,000. The polyol compounds percentage in binding solution can be up to 50% (v/v), but for all practical applications, it will be 1-30% (v/v). The polyol compounds are to ensure the complete miscibility of lysed components and if the proteinase K lysis is complete, the polyol percentage can decrease to 1%. The buffers known in state of art include bicine, tricine, Tris, HEPES, CHAPS, phosphate, acetate, MES, pyridine, piperazine, Bis-tris, PIPES, ACES, BES, TES, borate, TAPS, CHES, CAPS, ethanolamine, piperidine etc in the range of pH 5-12, preferably in the range of 7-10 can be used for preparing binding buffer and the buffer presence is not mandatory, but depending on the sample type, sample volume, temperature, lysis buffer composition, it can be used. If buffering salts are used, their concentration can vary from 1-200 mM, preferably 1-100 mM, and most preferably 5-50 mM. The concentration described above is the concentration of binding solution and after addition to lysis buffer the concentration will change depending on the composition of lysis buffer. Also, pH defined above is for the pH of the binding buffer when it was made and upon addition to lysis buffer the pH of the mixed solution (lysis buffer+binding buffer) could change. Though alcohols like methanol, ethanol, and propanol are not polyols, they can also be used in preparation of binding buffer. In general any water-soluble liquid with a functional group of acid, amine, alcohol, phenol, amide, ester etc as one of the functional groups can be used.

Wash Buffers:

A washing buffer is a solution, which will selectively wash the non-nucleic acid components from the cotton. If the clinical sample is blood, after binding, cotton will be brown in color and to remove color it was that found a percentage of ethanol in wash buffer (called wash buffer 1) helps. Particularly first wash was done with a buffer or water containing 1-99% (v/v), preferably 30-70% (v/v), more preferably 50% (v/v) ethanol. If required multiple aqueous ethanol washes can be given to get rid of non-nucleic acid components and it could depend on the sample. Methanol, n-propanol, 2-propanol, glycerol, PEG, PPG, ethylene glycol, propylene glycol or any other water-soluble alcohol can replace the ethanol in the wash solution. A wash buffer 2 can be used where in a mono or divalent cation is present along with wash buffer 1 as its composition. It is also possible that, wash buffer 1 and 2 can have same composition and comprise of water, an alcohol and a mono or divalent cation. The number of times cotton washed with wash buffers 1&2 can be 0-10 and ideally in the range of 1-3. Subsequent washes usually will be with deionized water and the number of washes can be one to ten, preferably 2 to 5 and more preferably 3-5. The deionized water used in washing step can be replaced with DNase, RNase free water, or MilliQ water or filtered water or tap water or ground water. We observed an initial wash with aqueous alcohol tends to remove most of the non-nucleic acid components and then followed by multiple water (100% water) washes to get rid of residual alcohol. The water washes ensure that the nucleic acids obtained are PCR ready with no or minimal PCR inhibitors. The wash buffers can optionally contain salts like MgCl2, CaCl2, NaCl, KCl, or buffers like bicine, tricine, Tris, HEPES, CHAPS, phosphate, acetate, MES, pyridine, piperazine, Bis-tris, PIPES, ACES, BES, TES, borate, TAPS, CHES, CAPS, ethanolamine, piperidine etc in the range of pH 5-12. The buffer or salt a combination of them could be in the concentration of 1-1000 mM, preferably in the range of 20-200 mM and more preferably around 100 mM.

Elution Buffer:

Any warm (45-99° C.) aqueous buffer solution could elute nucleic acids from cotton. The elution pH was found to be crucial, but preferably in the range of 8-11 and elution should be done at a temperature between 45-99° C. for complete recovery of nucleic acids. The deionized water used in buffer making in elution step can be replaced with DNase, RNase free water, or MilliQ water or filtered water or tap water or ground water. The buffers known in the state of art include bicine, tricine, Tris, HEPES, CHAPS, phosphate, acetate, MES, pyridine, piperazine, Bis-tris, PIPES, ACES, BES, TES, borate, TAPS, CHES, CAPS, ethanolamine, piperidine etc in the range of pH 5-12 can be used for elution, though the most preferred ones will be with pKa in the range of 7-10. Whenever cotton is used for elution of bound nucleic acids, the elution buffer should be warm and for practical considerations in the range of 45-99° C. This is in stark contrast to most of the literature reported methods wherein the elution is done at warm condition using deionized water, but the nucleic acids bound to cotton cannot be eluted completely with warm water and a buffer or salt presence is critical. The salt can be MgCl2, CaCl2, NaCl, KCl, etc in the concentration of 0-100 mM, preferably in the range of 5-50 mM. The buffer can be selected from the group of buffers namely bicine, tricine, Tris, HEPES, CHAPS, phosphate, acetate, MES, pyridine, piperazine, Bis-tris, PIPES, ACES, BES, TES, borate, TAPS, CHES, CAPS, ethanolamine, piperidine.

Recovery of Nucleic Acids:

With the current system, nucleic acids recovery is dependent on the lysis buffer, binding buffer, wash buffers and elution buffer and the combinations used. Depending on the combination, nucleic acid recovery could be comparable to any silica based nucleic acid extraction system. It was also observed that with low titer samples, the efficiency of our cotton-based nucleic acid extraction approach is sometimes better than silica.

Quantity of Cotton:

Quantity of cotton is dependent on the volume of clinical sample and for samples in the range of 1-300 µl, 5-30 mg of cotton was found to be adequate. For volumes of samples in the range of milliliters, a 50 mg or more of cotton may be essential. Overall 1 milligram to 10 grams of cotton is enough to extract nucleic acids from any clinical, environmental or field samples.

Price of Each Assay:

As the cotton used in this protocol is surgical cotton available commercially in any drug store or retail store (could be autoclaved or subjected to purification), the price of the each nucleic acid extraction is minimal and one of the cheapest reported to date in the literature. Again, considering the elimination of accidental PCR inhibitors presence in nucleic acid elutes, simplicity and adaptability to POC use, ease of automation, etc makes this approach superior and cost per extraction is probably an added bonus.

Safety of Components & Disposal of Solutions:

The cotton based nucleic acid extraction system utilizes most of the buffers of aqueous origin with which the waste can be disposed safely and effectively by a state of art person. The cotton can be packed in a cartridge and all the lysis, binding, wash solutions can be trapped in the cartridge for POC use with which the health-worker or analyst has no need to dispose the waste and the cartridge will be self-contained.

Uses of Extracted Nucleic Acids:

Extracted nucleic acids using the cotton protocol described in this embodiment can be ready to be used in a PCR or RT-PCR. Other applications of the described cotton protocol are for recovery of nucleic acids from a clinical sample for archiving, storage, further biochemical and molecular biology use etc. The extracted nucleic acids can be used for any biochemical or molecular biological application, which a person in the state of the art will discover from time to time.

Use of Cotton in a Form Suitable for Nucleic Acid Extraction:

This embodiment is to extract nucleic acids in 'PCR ready form' using cotton with minimal equipment requirement like centrifuge or other spinning equipment. Cotton can be packed in any form suitable for nucleic acid extraction depending on the quantity of the sample, nature of the sample and origin of the sample. Preferably, the nucleic acids were obtained in a solution or emulsion, which will be processed according to the described lysis, binding, washing and elution systems. Hence, cotton packing is a crucial part of nucleic acid extraction and any nature in which cotton could come in contact with solution containing nucleic acids is considered to be part of this disclosure. The FIGS. 1-3 illustrate some ways in which the cotton can be packed, but it should not be construed as limiting in any way. In a simple terms cotton is packed in such a way that nucleic acid containing solution comes in contact with cotton or cotton comes in contact with liquid and is considered to be part of this disclosure.

In another embodiment, the cotton can be packed in a modified plastic 1 mL pipette tip, modified plastic 2 mL pipette tip, 15 mL falcon tube, 50 mL falcon tube, 1.5 mL eppendorf tube, 2 mL eppendorf tube, 5 mL borosilicate glass test tube, 4 mL screw cap plastic vial, 3 mL plastic Pasteur pipette, glass Pasteur pipette, glass Pasteur pipette with a rubber bulb, plastic Pasteur pipette with rubber bulb, glass pipette with a rubber and plastic mould as bulb, 2 mL glass vial with a plastic cap, disposable and autoclaved 10 mL plastic syringe, a plastic mould attached to 5 mL syringe, a disposable unit attached to 50 mL syringe etc. The cotton also can be made as a cotton swab and the swab can be man made or machine made. The cotton swab shown is FIG. 3 [e] made up of viscose and any cotton-blended polymer (1 to 100%), or chemically or physically modified cotton (1 to 100%) is considered to be part of this disclosure.

Use of Cotton to Store a Clinical Sample:

The cotton can be exposed to sample directly and being absorbent, the cotton will stabilize and store the sample in a safe form. The safe form is defined as a means in which the added sample's nucleic acid content is not degraded significantly. The binding can be in a reversible fashion, where the nucleic acids can be extracted using the nucleic acid extraction protocol described in this embodiment. The cotton can be optionally embedded with a stabilizer, which will improve the stability of sample and sample constituents. Optionally, the cotton can be embedded with an enzyme or a chemical or the lysis buffer reported in this protocol or lysis buffer containing proteinase K, or proteinase K along with stabilizing buffer salts. The cotton could be EDTA treated, sodium azide treated, base treated, acid treated, lysis buffer treated, honey treated, any antibacterial agent treated, any antimicrobial agent treated, any antiviral compound treated or treated with EDTA and sodium azide, antibacterial, antimicrobial, antiviral, anticoagulants, stabilizers of clinical samples known in the state of art, honey, or any combination thereof. The volume of sample added to cotton to store can be any volume, but for all practical purposes it can be 1 µl to 20 mL and the quantity of cotton used can be any amount and for all practical purposes it can be 1 mg to 10 grams. When sample is collected, it can be done on a lysis buffer impregnated cotton and is also considered to be part of this disclosure.

Method of Use of Cotton Packed System for Nucleic Acid Extraction:

Cotton packed in a device as exemplified in FIG. 1-3 using the reported nucleic acid extraction protocol described in this embodiment. The mechanism by which cotton was made to interact with the lysis, binding, washing and elution systems described in this embodiment can be heating, shaking, vortexing, stirring, constant movement, pipetting, or any other means by which a solid and liquid are made to interact. Essentially, the liquid containing nucleic acid will come in contact with cotton fibers.

In another embodiment, the present method is one of the simplest & most flexible nucleic acid extraction protocols reported in literature. Almost all literature methods require a centrifuge to spin down contents, or magnet to hold magnetic particles in intact position or both and the method reported in this embodiment completely eliminates the need of centrifuge or a magnet. Existing nucleic acid protocols have limit on the volume of sample or require multiple processing for higher volumes of samples. This protocol can process virtually any quantity of sample (for practical purposes, 1 µl to 20 mL) in almost same time using single disposable extraction system. The present method produces nucleic acids immediately ready for further characterization and downstream processing such as PCR, sequencing or blotting. The simplicity of this system makes it equally suited for point of care (POC) or established laboratories, first of a kind reported in literature.

The cotton protocol described in this embodiment has salient features like elimination of use of centrifuge, minimal user to user variation, comparable efficiency to silica protocols, ease of use compared to any existing nucleic acid protocol, ability to process any quantity of sample, proper recovery of nucleic acids, ability to pick low titer samples, ease of automation, suited for both established hospital settings & point of care setups and high consistency in recovery & quality of nucleic acids.

In another embodiment, the method described in this disclosure employs fibrous materials like cotton to extract nucleic acids from virtually any clinical or analytical sample of biological origin in a PCR or reverse transcriptase-PCR (RT-PCR) or sequencing or blotting ready format. The procedure comprises lysing, binding of nucleic acids to cotton, washing the nucleic acid bound cotton with aqueous solutions, and elution of nucleic acids in a buffer with salt like KCl. A typical lysis buffer in silica or non-silica protocols contains some tetra or di basic ions like EDTA (chelating agents), which bind to the iron in blood. In this reported protocol, a high concentration of EDTA (10-300 mM) is added to create an environment wherein all the nucleic acids selectivity bind to cotton. Usually lysis buffer pH is adjusted to 6 to enable the binding to a matrix (silica or non-silica), where most of the proteins and other components are neutral or positive in charge where as nucleic acid is still negatively charged and interacts with the matrix. In the current system, binding pH should be basic (pH 8-11) and the excess of negatively charged EDTA (10-300 mM) itself acts as a buffer and brings the pH to around 8. Ours is the first protocol in which nucleic acids are lysed and can be bound to a matrix at basic pH. The binding buffer can be water, any aqueous buffer having pH in the range of 3-11, or water containing polyethylene glycol (PEG, 1-30%) or glycerol (1-30%) or polypropylene glycol (PPG, 1-30%) or ethylene glycol (1-50%) or propylene glycol (1-50%) or any water-soluble alcohol or any combination of the above. The binding buffer is to ensure the dilution of lysis buffer salts, enhance the binding of nucleic acids in EDTA rich atmosphere and solubilize the lysed particles. The reported protocol can tolerate a wide range of buffers with different pH for binding and this is also first time in literature that binding buffer pH or composition is so flexible. The longer sample processing times, limit on sample volume and non-feasibility of quantification of nucleic acids are associated drawbacks with FTA cards, which are not present with the nucleic acid extraction protocol reported in this embodiment using cotton. Finally, all the reported literature protocols do elution in an aqueous buffer or water at room temperature or occasionally at elevated temperature, and our nucleic acid washing is with water at room temperature and elution at elevated temperature (50-99° C.). Using the protocol and matrix defined in this embodiment, a hot deionized water will not elute all the bound nucleic acids and presence of a buffer or salt or a combination of them is a must. This is also in stark contrast to literature nucleic acid extraction protocol, which can elute bound nucleic acids from matrix in hot deionized water (both silica and non-silica protocols allow hot water elution of nucleic acids). The elution buffer could be anywhere between pH 8-10, indicating that elution pH is flexible and some concentration of salt like KCl is preferred for efficient elution of bound nucleic acids from cotton.

In another embodiment, in the methods below, cotton & other cotton-based fibrous materials were used in quantitative extraction of nucleic acids under special lysis, binding, washing and elution conditions, which are unique for elution nucleic acids from cotton. The present disclosure in one aspect provides a rapid nucleic acid isolation system from any environmental, clinical, bacterial, fungal, and animal origin using cotton. The samples can be cell lysates, body fluids, plants, tissues, and bacterial cells & cell lysates. Cotton & viscose are fibrous materials obtained naturally & artificially respectively, which were found to bind to nucleic acids under given conditions. The process of nucleic acid binding and selective retention of nucleic acids on the cotton and release of nucleic acids under specific elution conditions is exemplified by the DNA and RNA.

In another embodiment, in a typical DNA extraction from a clinical sample like blood, the blood was lysed with a lysis buffer comprising of guanidine thiocyanate, EDTA, a buffer like Tris, a detergent like triton X-100, and optionally with urea, a polyol, a monovalent salt containing group IA cation and/or a divalent salt containing a group IIA cation, and protein cleaving enzymes like proteinase K. The Guanidine thiocyanate can be anywhere between 0.1 to 7M in concentration. Guanidine thiocyanate can be replaced with guanidine hydrochloride in some application and its concentration also could vary from 1 to 6 M. Urea is used to denature the proteins and it will complement the function of guanidine salts and could vary between 0 to 7 M. Typically most of the literature reported lysis protocols for blood contain EDTA in the range of 20 mM. Our lysis buffer could tolerate significantly higher amounts of EDTA in the range of 10-300 mM, preferably around 100 mM range for efficient nucleic acid binding to cotton. The EDTA concentration can be manipulated for other nucleic acids like RNA and PNA, but in general, a higher concentration of EDTA was found to help in improvement of cycle times (Ct) and signal intensities in PCR and RT-PCR. The significantly higher concentration of EDTA helps in arresting the iron present in hemoglobin (for blood), prevents any DNase activity, and creates a highly negative atmosphere wherein nucleic acid can bind to the cotton. The important aspect of it is that, addition of significantly higher concentration of EDTA in the buffer makes the pH of the buffer basic and as far as our knowledge is concerned, this embodiment is the first example wherein nucleic acid binding to a matrix is done under basic conditions. Importantly, the binding pH of the solution has to be basic to enable nucleic acid binding to cotton, as at very acidic pH, there is chance of EDTA precipitating out of the lysis buffer and hence a pH above 8 is preferred for binding. Magnesium chloride is typically used in higher concentrations to deactivate RNase activity and hence, in nucleic acid lysis protocol it could be used. Tris is the choice of buffer for lysis, and we found 0-100 mM can be used and typically around 20 mM is the optimal. The use of polyol in the lysis or binding buffer is to increase the activity of Proteinase K and to improve the solubility of cleaved proteins. The polyol percentage in the lysis buffer could be 0-30% (v/v). All these buffers were made in deionized water and for RNA application, the water could be treated with DEPC and autoclaved. The proteinase K lysis can be done ahead of the addition of the above described lysis buffer for blood, sputum, saliva etc and along with lysis buffer for urine, sweat, etc. The proteinase K treatment was found to be effective in the mentioned lysis buffer and hence, this treatment can be ahead of lysis buffer addition or could be along with lysis buffer for any kind of clinical sample containing nucleic acids.

In another embodiment, binding buffer, which was added after lysis to initiate the binding of nucleic acids with cotton was found to be very flexible in terms of composition. Binding buffer is so flexible that, just addition of water is enough to dilute the concentration of salts in lysis buffer and good binding of nucleic acids to cotton was observed. Cotton can be placed to interact during the lysis or after addition of binding buffer. Binding buffer composition can be of any pH between 5 to 12, preferably in the range of 7-10. For complex samples like blood, sputum or saliva, the binding buffer can have a certain percentage of polyols compounds like PEG, glycerol, PPG, ethylene glycol, propylene glycol etc. Traditionally used binding solutions (for silica based nucleic acid systems) like ethanol or aqueous ethanol were found to decrease binding affinity of nucleic acids to cotton. i.e. Presence of ethanol during binding step was found to decrease the efficiency of nucleic acid binding to cotton.

In another embodiment, a washing buffer is a solution, which will selectively wash the non-nucleic acid components from the cotton. If the clinical sample is blood, after binding, cotton will be brown in color and to remove color it was that found a percentage of ethanol in wash buffer (called wash buffer 1) helps. Particularly first wash was done with a buffer or water containing 10-90%, preferably 30-70%, more preferably 50% ethanol. Methanol, n-propanol, isopropanol, glycerol, PEG, PPG, ethylene glycol, propylene glycol or any other water-soluble alcohol can replace the ethanol in the wash solution. A wash buffer 2 can be used where in a mono or divalent cation is present along with wash buffer 1 as its composition. It is also possible that, wash buffer 1 and 2 can have same composition and comprise of water, an alcohol and a mono or divalent cation. The number of times cotton washed with wash buffers can be 0-10 and ideally in the range of 1-3. Subsequent washes usually will be with deionized water and the number of washes can be one to ten, preferably 2 to 5 and more preferably 3-5. The deionized water used in washing step can be replaced with DNase, RNase free water, or MilliQ water or filtered water or tap water or ground water.

In another embodiment, elution of nucleic acids from cotton can be done with any aqueous buffer. The buffer concentration needs to be between 1 to 200 mM, preferably 5-50 mM, more preferably, 30-70 mM in the elution buffer. The buffers known in state of art include bicine, tricine, Tris, HEPES, CHAPS, phosphate, acetate, MES, pyridine, piperazine, Bis-tris, PIPES, ACES, BES, TES, borate, TAPS, Ethanolamine, CHES, CAPS, ethanolamine, piperidine etc in the range of pH 5-12, preferably in the range of 7-10, more preferably in the range of 8-10, will work for elution of nucleic acids from cotton under hot condition. Nucleic acid elution from cotton needs to be done at an elevated temperature between 50 to 100° C., preferably at 70-95° C., more preferably at around 85° C.

In another embodiment, purified nucleic acids can be 10-100% pure, and usually will be PCR ready. The purity of nucleic acids is dependent on the optimum combination of lysis, binding, washing and elution buffers and the matrix for purification (cotton or cotton derivatives or cotton-blended materials). We observed that, FTA cards or cellulose bound particles, or cellulosic filter papers are not efficient under these buffer combinations indicating that, the cotton is different from other forms of cellulose with respect to interaction with nucleic acids. In related methods, present disclosure provides a means to isolate nucleic acids from a sample containing nucleic acids using cotton or cotton derivatives or cotton-blended materials as the solid matrix using the following general protocol.

a) The sample containing nucleic acids was added to lysis buffer. The lysis buffer comprises of guanidine thiocyanate, EDTA, Tris, a detergent, and optionally with urea, a polyol, a monovalent salt containing group IA cation and/or a divalent salt containing a group IIA cation, and proteinase K. The nucleic acid sample & lysis buffer were mixed and heated at 50-95° C. for 1-20 min.

b) A binding buffer is added to the above solution and it could be water, a buffer with pH between 4-11, or a solution containing a polyol. The volume of the binding buffer could be 0.1-10 times of the lysis buffer volume.

c) The above solution was made to interact with cotton preferably at room temperature for few seconds to few minutes.

d) Then cotton was washed specifically (1$^{st}$ wash) with a wash buffer comprising of aqueous alcohol or water alone.

e) Above cotton was subsequently washed with water or a buffer till the residual alcohol is removed from the cotton.

f) The nucleic acids were eluted with a buffer comprising of salt like KCl (Group IA or Group IIA cation containing salts) and/or bicine like buffer and the eluted nucleic acids are usually ready to be used in PCR or RT-PCR.

The present disclosure is further elaborated with the help of the following table which provides for a comparative account between the method used in the present disclosure and those used in the prior art. The table compares some of the important aspects with regards to the various methods used for the characterization of methods used towards isolation of nucleic acids.

TABLE 1

Comparative account of important aspects involved in isolation of Nucleic Acids.

| S. No | Property | Nucleic acid extraction using cotton | Nucleic acid extraction based on cellulose matrix | Nucleic acid extraction using commercial silica columns | Nucleic acid extraction using magnetic nano particles coated with silica |
|---|---|---|---|---|---|
| 1 | Lysis buffer pH above 8 | Yes | No | No | No |
| 2 | Single protocol for DNA/RNA | Yes | Possible | Possible, but different protocols are usually given | Possible |
| 3 | Elution of nucleic acids with water/buffer at pH 7 | No | Yes | Yes | Yes |
| 4 | 100% aqueous wash of matrix bound nucleic acids | Yes | possible | No | No |
| 5 | Automated nucleic acid processing | Yes | Not reported in literature | Not reported in literature | Prototypes exist in literature |
| 6 | Use of Centrifuge | No | Yes | Yes | In some protocols |
| 7 | Aerosol generation during protocol | No | Yes | Yes | In some protocols |
| 8 | Suitability for point of care | Yes | No, Needs an additional laboratory based sample processing | No, requires a centrifuge and generates aerosols | No, Requires bulky instruments |
| 9 | RT-PCR suitable nucleic acid extraction | Yes | Yes | Yes | Yes |
| 10 | Ability to process different samples like blood, sputum, serum, saliva, tissues etc with minimal sample pre-processing | Yes | No | No | No |
| 11 | Typical time taken for isolation of Nucleic Acid | 8-12 mins | 20-30 mins | 15-20 mins | 15-20 mins |
| 12 | Standard costs involved towards isolation of Nucleic Acid (cost of reagents, matrix, and other components of kit) | Rs. 10-30 | Rs. 50-100 | Rs. 150-500 | Rs. 100-500 |

The technology of the instant disclosure is further elaborated in detail with the help of following examples. However, the examples should not be construed to limit the scope of the disclosure.

General Methodology:

Nucleic acid containing solution was brought in contact with cotton preferably at room temperature and the non-nucleic components were washed off from cotton using a series of washes comprising of aqueous alcohol and water. The nucleic acids from cotton were eluted using an aqueous buffer comprising of a salt at elevated temperature. Eluted nucleic acids will be ready for further processing or for the PCR. The following examples are given with cotton packed in a 1 mL pipette tip used commonly in research labs. But as a state of art person may realize that the cotton can be packed in any form where there is a chance for a liquid to contact with it. Essentially, any thing with an inlet and an outlet and in between cotton can be packed is considered to be part of this disclosure.

EXAMPLE-1

DNA Extraction from Blood a) 50 μl blood was added to 75 μL lysis buffer (30 μL of 10 mg/mL proteinase K, 5.6 M guanidine thiocyanate, 100 mM EDTA, 20 mM Tris, 0.01% triton X-100). The resultant solution was heated to 60° C. and left at that temperature for 3 min. Then the solution was heated at 85° C. for 2 min.

b) 150 μL of binding buffer (water with 0.1 g/mL of PEG 6000) was added to the above solution.

c) A 1 mL plastic dropper packed with 8 mg cotton (cotton dropper, as shown in FIG. 2[a]) was made to interact with above solution.

d) Then cotton dropper was washed with 2 mL each of wash buffer 1 (50% ethanol) and wash buffer 2 (50% ethanol containing 100 mM $MgCl_2$).
e) The cotton tip was washed with water (3×1 mL).
f) The nucleic acids were eluted in 100 uL elution buffer (10 mM bicine, 10 mM KCl, pH 9.8) at 95° C.

EXAMPLE-2

DNA Extraction from Blood a) 100 μl blood was added to 150 μL lysis buffer (40 μL of 10 mg/mL proteinase K, 5.6 M guanidine thiocyanate, 100 mM EDTA, 20 mM Tris, 0.01% triton X-100). The resultant solution was heated to 60° C. and left at that temperature for 3 min. Then the solution was heated at 85° C. for 2 min.
b) 300 μL of binding buffer (water with 0.1 g/mL of PEG6000) was added to the above solution.
c) A 1 mL molded pipette tip packed with 10 mg cotton (cotton tip, as shown in FIG. 3[c]) was made to interact with above solution.
d) Then cotton tip was washed with 1 mL wash buffer 1 (50% ethanol) and 2 mL of wash buffer 2 (50% ethanol containing 100 mM $MgCl_2$).
e) The cotton tip was washed with water (3×1 mL).
f) The nucleic acids were eluted in 200 uL elution buffer (10 mM bicine, 10 mM KCl, pH 9.8) at 95° C.

EXAMPLE-3

DNA Extraction from Blood a) 100 μl malaria (*P. falciparum*) parasite containing blood was added to 150 μL lysis buffer (40 μL of 10 mg/mL proteinase K, 5.6 M guanidine thiocyanate, 100 mM EDTA, 20 mM Tris, 0.01% triton X-100). The resultant solution was heated to 60° C. and left at that temperature for 3 min. Then the solution was heated at 85° C. for 2 min.
b) 300 μL of binding buffer (water with 0.1 g/mL of PEG6000) was added to the above solution.
c) A 1 mL molded pipette tip packed with 10 mg cotton (cotton tip, as shown in FIG. 3[c]) was made to interact with above solution.
d) Then cotton tip was washed with 1 mL of wash buffer 1 (50% ethanol)
e) The cotton tip wash washed with 2 mL of wash buffer 2 (50% ethanol containing 100 mM $MgCl_2$).
f) The cotton tip was washed with water (3×1 mL).
g) The nucleic acids were eluted in 200 uL elution buffer (10 mM bicine, 10 mM KCl, pH 9.8) at 95° C.

EXAMPLE-4

RNA Extraction from Blood a) 50 μl Chikungunya positive blood was added to 75 μL lysis buffer (30 μL of 10 mg/mL proteinase K, 5.6 M guanidine thiocyanate, 100 mM EDTA, 20 mM Tris, 0.01% triton X-100). The resultant solution was heated to 60° C. and left at that temperature for 3 min. Then the solution was heated at 85° C. for 2 min.
b) 150 μL of binding buffer (water with 0.1 g/mL of PEG6000) was added to the above solution.
c) A 1 mL pipette tip packed with 10 mg cotton was made to interact with above solution.

d) Then cotton tip was washed specifically with a 1 mL wash buffer 1 (50% ethanol containing 50 mM $MgCl_2$).
e) The cotton tip was washed with water (3×1 mL).
f) The nucleic acids were eluted in 200 uL elution buffer (10 mM bicine, 10 mM KCl, pH 9.8) at 95° C.

EXAMPLE-5

DNA Extraction from Saliva a) 50 μl saliva was added to 100 μL lysis buffer (10 μL of 10 mg/mL proteinase K, 5.6 M guanidine thiocyanate, 200 mM EDTA, 20 mM Tris, 0.01% triton X-100). The resultant solution was heated to 60° C. and left at that temperature for 3 min. Then the solution was heated at 85° C. for 2 min.
b) 250 μL of binding buffer (10% glycerol in water) was added to the above solution.
c) A 1 mL molded pipette tip packed with cotton (cotton tip, as shown in FIG. 3[c]) was made to interact with above solution.
d) Then cotton tip was washed specifically with 3 mL wash buffer 1 (50% ethanol containing 200 mM $MgCl_2$).
e) The cotton tip was washed with water (3×1 mL) by pipetting the liquid three times during each washing.
f) The nucleic acids were eluted in 250 μL elution buffer (10 mM bicine, 50 mM KCl, pH 9.8) at 95° C.

EXAMPLE-6

RNA Extraction from Blood a) 100 μl chikungunya positive blood was added to 150 μL lysis buffer (40 μL of 10 mg/mL proteinase K, 5.6 M guanidine thiocyanate, 100 mM EDTA, 20 mM Tris, 0.01% triton X-100). The resultant solution was heated to 60° C. and left at that temperature for 3 min. Then the solution was heated at 85° C. for 2 min.
b) 300 μL of binding buffer (water with 0.1 g/mL of PEG 6000) was added to the above solution.
c) A 1 mL molded pipette tip packed with 10 mg cotton (cotton tip, as shown in FIG. 3[c]) was made to interact with above solution.
d) Then cotton tip was washed specifically with 1 mL wash buffer 1 (50% ethanol) and 2 mL of wash buffer 2 (50% ethanol containing 50 mM $MgCl_2$).
e) The cotton tip was washed with water (2×1 mL).
f) The nucleic acids were eluted in 100 uL elution buffer (10 mM bicine, 10 mM KCl, pH 9.8) at 95° C.

EXAMPLE-7

RNA Extraction from Blood a) 50 μl Chikungunya positive blood was added to 75 μL lysis buffer (40 μL of 10 mg/mL proteinase K, 5.6 M guanidine thiocyanate, 80 mM EDTA, 20 mM Tris, 0.01% triton X-100). The resultant solution was heated to 55° C. and left at that temperature for 3 min. Then the solution was heated at 70° C. for 2 min.
b) 150 μL of binding buffer (water with 0.1 g/mL of PEG 8000) was added to the above solution.
c) A 2.5 mL synringe packed with 10 mg cotton (cotton syringe, as shown in FIG. 1[a]) was made to interact with above solution.

d) Then cotton tip was washed specifically with a 1 mL wash buffer 1 (50% ethanol) and 2 mL of wash buffer 2 (50% ethanol containing 50 mM $MgCl_2$).
e) The cotton syringe was washed with water (3×1 mL).
f) The nucleic acids were eluted in 100 uL elution buffer (10 mM bicine, 10 mM KCl, pH 9.8) at 95° C.

EXAMPLE-8

DNA Extraction from Sputum a) 100 μl sputum was added to 150 μL lysis buffer (40 μL of 10 mg/mL proteinase K, 5.6 M guanidine thiocyanate, 100 mM EDTA, 20 mM Tris, 0.01% triton X-100). The resultant solution was heated to 60° C. and left at that temperature for 5 min. Then the solution was heated at 75° C. for 2 min.
b) 300 μL of binding buffer (water with 0.1 g/mL of PEG 6000) was added to the above solution.
c) A 5 mL bellow pipette packed with 10 mg cotton (cotton bellow, as shown in FIG. 2[b]) was made to interact with above solution.
d) Then cotton tip was washed specifically with a 1 mL wash buffer 1 (50% ethanol) and wash buffer 2 (50% ethanol containing 50 mM $MgCl_2$).
e) The cotton bellow was washed with water (3×1 mL).
f) The nucleic acids were eluted in 100 uL elution buffer (10 mM tricine, 10 mM KCl, pH 9.8) at 95° C.

EXAMPLE-9

DNA extraction from serum a) 50 μl serum was added to 75 μL lysis buffer (60 μL of 10 mg/mL proteinase K, 5.6 M guanidine thiocyanate, 100 mM EDTA, 20 mM Tris, 0.01% triton X-100). The resultant solution was heated to 60° C. and left at that temperature for 3 min. Then the solution was heated at 85° C. for 2 min.
b) 150 μL of binding buffer (water with 0.1 g/mL of PEG 6000) was added to the above solution.
c) A 1 mL molded pipette tip packed with 10 mg cotton (cotton tip, as shown in FIG. 3[c]) was made to interact with cotton.
d) Then cotton tip was washed specifically with 1 mL of wash buffer 1 (50% ethanol) and 2 mL of wash buffer 2 (50% ethanol containing 50 mM $MgCl_2$).
e) The cotton tip was washed with water (3×1 mL).
f) The nucleic acids were eluted in 200 uL elution buffer (10 mM bicine, 10 mM KCl, pH 9.8) at 95° C.

EXAMPLE-10

RNA Extraction from Serum a) 100 μl chikungunya positive serum was added to 150 μL lysis buffer (40 μL of 10 mg/mL proteinase K, 5.6 M guanidine thiocyanate, 100 mM EDTA, 20 mM Tris, 0.01% triton X-100). The resultant solution was heated to 60° C. and left at that temperature for 3 min. Then the solution was heated at 85° C. for 2 min.
b) 300 μL of binding buffer (water with 0.1 g/mL of PEG6000) was added to the above solution.
c) A 1 mL molded pipette tip packed with 10 mg cotton (cotton tip, as shown in FIG. 3[c]) was made to interact with cotton.
d) Then cotton tip was washed specifically with a 3 mL wash buffer 1 (50% ethanol containing 50 mM $MgCl_2$).
e) The cotton tip was washed with water (3×1 mL).
f) The nucleic acids were eluted in 200 uL elution buffer (10 mM bicine, 10 mM KCl, pH 9.8) at 95° C.

EXAMPLE-11

DNA Extraction from Sputum a) 50 μl sputum was added to 150 μL lysis buffer (40 μL of 10 mg/mL proteinase K, 5.6 M guanidine thiocyanate, 100 mM EDTA, 20 mM Tris, 0.01% triton X-100, pH 9.5). The resultant solution was heated to 60° C. and left at that temperature for 3 min. Then the solution was heated at 85° C. for 6 min.
b) 150 μL of binding buffer (water with 0.1 g/mL of PEG 6000) was added to the above solution.
c) 10 mg cotton was made to interact with above solution
d) Then cotton was washed specifically with a 3 mL wash buffer 1 (50% ethanol containing 50 mM $MgCl_2$).
e) The cotton was washed with water (3×1 mL).
f) The nucleic acids were eluted in 100 uL elution buffer (10 mM bicine, 10 mM KCl, pH 9.8) at 95° C.

EXAMPLE-12

DNA Extraction from Sputum a) 50 μl sputum was added to 75 μL lysis buffer (40 μL of 10 mg/mL proteinase K, 5.6 M guanidine thiocyanate, 100 mM EDTA, 20 mM Tris, 0.01% triton X-100, pH 9.5). The resultant solution was heated to 60° C. and left at that temperature for 5 min.
b) 150 μL of binding buffer (water with 0.1 g/mL of PEG 6000) was added to the above solution.
c) 10 mg cotton was made to interact with above solution.
d) Then cotton was washed specifically with a 3 mL wash buffer 1 (50% ethanol containing 100 mM $MgCl_2$).
e) The cotton was washed with water (3×1 mL).
f) The nucleic acids were eluted in 100 uL elution buffer (10 mM bicine, 10 mM KCl, pH 9.8) at 95° C.

EXAMPLE-13

RNA Extraction from Tissue a) 50 μl rabies positive tissue was added to 175 μL lysis buffer (40 μL of 10 mg/mL proteinase K, 5.6 M guanidine thiocyanate, 100 mM EDTA, 20 mM Tris, 0.01% triton X-100, pH 9.5), vortexed for 7 min and supernatant was transferred to a tube. The resultant solution was heated to 60° C. and left at that temperature for 3 min. Then the solution was heated at 75° C. for 3 min.
b) 350 μL of binding buffer (water with 0.1 g/mL of PEG 6000) was added to the above solution.
c) 20 mg cotton was made to interact with above solution.
d) Then cotton was washed specifically with a 3 mL wash buffer 1 (50% ethanol containing 100 mM $MgCl_2$).
e) The cotton was washed with water (3×1 mL).
f) The nucleic acids were eluted in 100 uL elution buffer (10 mM bicine, 10 mM KCl, pH 9.8) at 95° C.

EXAMPLE-14

RNA Extraction from Blood a) The lysis buffer, binding buffer, wash buffers and elution buffer were prepared in DEPC water.

b) A 50 μL of Chikungunya blood was placed in 50 μL of 10 mg/mL proteinase K and 250 μL lysis buffer (5.6 M guanidine thiocyanate, 20 mM EDTA, 20 mM Tris, 100 mM $MgCl_2$, 0.1% triton X-100). The tube was heated to 60° C. and left at that temperature for 3 min. Then the tube was heated at 80° C. for 2 min.
c) 1 mL of binding buffer (10% PEG 6000) was added to the above solution.
d) A 3 mL syringe packed with cotton (cotton syringe, as shown in FIG. 1[a]) was made to interact with solution by pulling the syringe lever back and forth five times.
e) Then cotton syringe was washed specifically with a 3 mL wash buffer 1 (50% ethanol containing 100 mM $MgCl_2$) by pulling the syringe lever back and forth seven times.
f) The cotton syringe was washed with water (3×2 mL) by pulling the syringe lever back and forth along with liquid three times during each washing.
g) The nucleic acids were eluted in 200 μL elution buffer (10 mM bicine, 10 mM KCl, pH 9.8) at 95° C. by pulling the syringe lever back and forth along with liquid two times.
h) The nucleic acids present in blood were obtained in PCR ready form and total protocol took about 9 minutes.

EXAMPLE-15

Peptide Nucleic Acids (PNA) Extraction a) 50 μl PNA containing standard solution was added to 75 μL lysis buffer (10 μL of 10 mg/mL proteinase K, 5.6 M guanidine hydrochloride, 100 mM EDTA, 20 mM Tris, 0.01% triton X-100, pH 9.5), vortexed for 7 min and supernatant was transferred to a tube. The resultant solution was heated to 60° C. and left at that temperature for 3 min. Then the solution was heated at 75° C. for 3 min.
b) 150 μL of binding buffer (water with 0.1 g/mL of PEG6000) was added to the above solution.
c) 10 mg cotton was made to interact with above solution.
d) Then cotton was washed specifically with a 3 mL wash buffer 1 (50% ethanol containing 100 mM $MgCl_2$).
e) The cotton was then washed with water (3×1 mL).
f) The protein nucleic acids were eluted in 100 uL elution buffer (10 mM bicine, 10 mM KCl, pH 9.8) at 95° C.

EXAMPLE-16

PCR Amplification

DNA/RNA samples purified by protocol of instant disclosure are subjected to PCR amplification followed by gel electrophoresis. The results are depicted in FIGS. 4, 5, 6, and 7. FIG. 4 provides comparative bands of DNA samples isolated and purified using viscose, commercial viscose swab, cotton packed in 1 ml pipette tip, commercial silica column and cotton swab. Similarly, FIG. 5 provides comparative bands of DNA samples purified by different protocols namely cotton packed in 1 mL pipette tip, cotton packed in 2 mL syringe, commercial silica column, and molecular weight marker.

Also, FIG. 6 provides comparative bands of DNA samples purified by different protocols namely molecular weight marker, commercial silica protocol, Cotton packed in 1 mL pipette tip, Whatman No 1 filter paper packed in a pipette tip and FTA card protocol.

Further, FIG. 7 provides for comparative bands of a 30 ct RNA sample amplified by RT-PCR, which were purified by different protocols. The protocols used different sources of the cotton matrix namely Surgical cotton, Autoclaved cotton, Sodium Hydroxide washed cotton, Hydrochloric Acid washed cotton and Absorbing cotton.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method for isolation of nucleic acid from a sample, said method consisting of the steps of:
    (a) adding lysis buffer having basic pH to the sample containing nucleic acid to obtain a lysed solution;
    (b) adding a binding buffer to the lysed solution obtained in step (a) to bind the nucleic acid to a cotton matrix at room temperature, wherein the binding buffer has a pH ranging from 8 to 11; and
    (c) washing with wash buffer and eluting the cotton matrix bound nucleic acid with an elution buffer to isolate and purify the nucleic acid,
    wherein the lysis buffer is selected from the group consisting of guanidine thiocyanate, guanidine hydrochloride, EDTA, Tris, detergent, polyol, monovalent salt containing group IA cation, divalent salt containing group IIA cation, protein digesting enzyme and combinations thereof,
    wherein the sample containing nucleic acid and the lysis buffer are mixed and heated at 50° C. to 95° C. for 1-20 minutes,
    wherein the lysis buffer has a pH ranging from about 8 to about 11;
    wherein the binding buffer comprises water; and
    where the elution buffer comprises water and a buffer or salt, the elution buffer having a temperature ranging from 45° C. to 99° C. and having pH ranging from 8 to 11.

2. The method as claimed in claim 1, wherein said nucleic acid is selected from the group consisting of DNA, RNA and PNA.

3. The method as claimed in claim 1, wherein said sample is a biological or non-biological sample.

4. The method as claimed in claim 3, wherein the biological sample is selected from the group consisting of blood, sputum, serum, saliva and tissue extracts and the non-biological sample is chemically synthesized PNA.

5. The method as claimed in claim 1, wherein said EDTA is of concentration ranging from about 10 mM to about 300 mM.

6. The method as claimed in claim 1, wherein said guanidine thiocyanate or said guanidine hydrochloride is of concentration ranging from about 0.1 M to about 7 M.

7. The method as claimed in claim 1, wherein said lysis buffer further comprises urea at a concentration ranging from about 0.01 M to about 7 M.

8. The method as claimed in claim 1, wherein said Tris is of concentration ranging from about 0.01 mM to about 100 mM.

9. The method as claimed in claim 1, wherein said polyol is of concentration ranging from about 0.01% to about 30% (v/v).

10. The method as claimed in claim 1, wherein said detergent is selected from the group consisting of sodium lauryl sulphate, sodium dodecyl sulphate, Triton X-100, NP-40, Tween 20 and combinations thereof and wherein the protein digesting enzyme is proteinase K.

11. The method as claimed in claim 1, wherein said binding buffer further comprises a polyol comprising water soluble polyol compounds selected from the group consisting of Poly-ethylene glycol, glycerol, Poly-propylene glycol, ethylene glycol and propylene glycol.

12. The method as claimed in claim 1, wherein said binding buffer further comprises a non-polyol comprising alcohols selected from the group consisting of methanol, ethanol, and propanol, or wherein the non-polyol is any water-soluble liquid with an acid, amine, alcohol, phenol, or ester functional group, and combinations thereof.

13. The method as claimed in claim 1, wherein said washing comprises a first wash with a washing buffer comprising about 1% to about 99% (v/v) of aqueous alcohol followed by multiple washes with 100% water.

14. The method as claimed in claim 13, wherein said aqueous alcohol is selected from the group consisting of ethanol, methanol, n-propanol, 2-propanol, glycerol, PEG, PPG, ethylene glycol and propylene glycol.

15. The method as claimed in claim 1, wherein said water is selected from the group consisting of deionized water, DNase free water, RNase free water, MilliQ water, filtered water, tap water, ground water and combinations thereof.

16. The method as claimed in claim 1, wherein said washing buffer comprises salts selected from the group consisting of $MgCl_2$, $CaCl_2$, NaCl and KCl, or buffers selected from a group consisting of bicine, tricine, Tris, HEPES, CHAPS, phosphate, acetate, MES, pyridine, piperazine, Bis-tris, PIPES, ACES, BES, TES, borate, TAPS, CHES, CAPS, ethanolamine and piperidine, having pH ranging from about 5 to about 12.

17. The method as claimed in claim 1, wherein said water is selected from the group consisting of deionized water, DNase free water, RNase free water, MilliQ water, filtered water, tap water, ground water and combinations thereof.

18. The method as claimed in claim 1, wherein said salt is selected from the group consisting of $MgCl_2$, $CaCl_2$, NaCl, KCl and combinations thereof in the concentration ranging from about 0.01 mM to about 100 mM.

19. The method as claimed in claim 1, wherein the cotton is selected from the group consisting of natural cotton, surgical cotton, clinical grade cotton, commercial cotton, spun cotton, water washed cotton, acid or base washed cotton, autoclaved cotton, buffer treated cotton having pH ranging from about 1 to about 14, salt solution treated cotton, organic solvent treated cotton, pressed cotton and processed cotton.

\* \* \* \* \*